United States Patent
Hansel et al.

(10) Patent No.: US 7,776,768 B2
(45) Date of Patent: Aug. 17, 2010

(54) PHTHALATE-FREE ISOCYANURATE PREPARATIONS

(75) Inventors: Jan-Gerd Hansel, Bergisch Gladbach (DE); Thomas Augustin, Köln (DE)

(73) Assignee: LANXESS Deutschland GmbH, Leverkusen (DE)

( * ) Notice: Subject to any disclaimer, the term of this patent is extended or adjusted under 35 U.S.C. 154(b) by 86 days.

(21) Appl. No.: 12/218,439

(22) Filed: Jul. 15, 2008

(65) Prior Publication Data

US 2010/0015873 A1    Jan. 21, 2010

(30) Foreign Application Priority Data

Jul. 26, 2007    (DE) .................. 10 2007 034 977

(51) Int. Cl.
*B32B 27/04* (2006.01)
(52) U.S. Cl. .................. 442/149; 442/158; 528/905
(58) Field of Classification Search .................. 442/149, 442/158; 428/160, 190, 317.7
See application file for complete search history.

(56) References Cited

U.S. PATENT DOCUMENTS

| 4,115,373 | A | 9/1978 | Henes et al. .................. 528/48 |
| 4,518,729 | A | 5/1985 | Breidenbach et al. ....... 524/101 |
| 5,204,391 | A | 4/1993 | Nakata et al. ................ 524/100 |
| 5,723,564 | A * | 3/1998 | Schmalstieg et al. .......... 528/73 |
| 6,652,774 | B2 * | 11/2003 | Zhou et al. ............. 252/182.24 |
| 6,936,678 | B2 | 8/2005 | Brahm et al. ................. 528/53 |
| 2004/0024213 | A1 * | 2/2004 | Brahm et al. ................ 544/193 |
| 2008/0287613 | A1 | 11/2008 | Simon et al. ................ 525/454 |

FOREIGN PATENT DOCUMENTS

| GB | 1455701 | 11/1976 |
| WO | WO2005/070984 | 8/2005 |

* cited by examiner

*Primary Examiner*—Lynda Salvatore
(74) *Attorney, Agent, or Firm*—Michael A. Miller

(57) ABSTRACT

The present invention relates to novel low-monomer-content, low-viscosity preparations composed of isocyanurates which contain isocyanate groups and of phthalate-free plasticizers, to their use as adhesion promoters for coating compositions based on plasticized polyvinyl chloride, and also to coatings and to coated substrates.

9 Claims, No Drawings

PHTHALATE-FREE ISOCYANURATE PREPARATIONS

The present invention relates to novel low-monomer-content, low-viscosity preparations composed of isocyanurates which contain isocyanate groups and of phthalate-free plasticizers, to their use as adhesion promoters for coating compositions based on plasticized polyvinyl chloride (PVC), and also to coatings and to coated substrates.

BACKGROUND OF THE INVENTION

It is known that the adhesion capability of plasticized PVC on substrates can be improved by adding, to the plasticized PVC, an adhesion promoter which contains isocyanate groups. This type of improved adhesion capability is important by way of example when the intention is to produce synthetic textile materials provided with a PVC covering. Preference is given to use, as adhesion promoters, of isocyanurates which contain isocyanate groups and which can be prepared by oligomerization, in particular trimerization, from diisocyanates. The diisocyanates most suitable for this purpose are the mixtures, which are readily available commercially, of the isomeric diisocyanatotoluenes (TDI), composed mainly of 2,4-diisocyanatotoluene (2,4-TDI) and 2,6-diisocyanatotoluene (2,6-TDI). These can easily be reacted almost completely to give isocyanurates which contain isocyanate groups. Almost complete reaction is necessary because operator safety and product safety require that the residual content of diisocyanates in the adhesion promoter preparation remains below 1.0% by weight. Diisocyanatodiphenylmethanes (MDI) are likewise readily available but are less suitable, and are more difficult than TDI to trimerize and can therefore lead to undesirably high residual content of diisocyanates. Isocyanurates which contain isocyanate groups based on MDI moreover exhibit poor solubility and have a tendency towards crystallization.

Isocyanurates which contain isocyanate groups are particularly easy to handle as adhesion promoters when they are used in the form of a solution in a plasticizer. In a practical method, the isocyanurates which contain isocyanate groups and are derived from TDI are likewise prepared in the plasticizer used as solvent. DE 24 19 016 A1 (GB 145 570 1A) describes by way of example these adhesion promoters and adhesion promoter preparations comprising plasticizer, and their preparation and their use.

Plasticizers are substances which on mixing with PVC, which is intrinsically hard and brittle, give a soft, tough material known as plasticized PVC. Examples of known plasticizers are the esters of phthalic acid, adipic acid or benzoic acid. Plasticized PVC can comprise large amounts of these plasticizers, sometimes more than 50% by weight of the plasticized PVC. Under service conditions, the plasticizer can separate at the surface or transfer into adjacent materials. The use of plasticized PVC therefore poses the risk of contamination of persons and of the environment by the plasticizer. In the light of these problems, a demand increasingly placed on the plasticizers used is that, with respect to humans, they are harmless and are not bioaccumulative.

According to the European Union Directive 2005/84/EG, the plasticizers di(2-ethylhexyl) phthalate, dibutyl phthalate and benzyl butyl phthalate can no longer be used in toys or baby products, and the plasticizers diisononyl phthalate, diisodecyl phthalate and di-n-octyl phthalate can no longer be used in toys or baby products which can be placed in children's mouths. In view of these restrictions, which many consumers may regard as worrying and difficult to understand, many producers are proceeding towards general elimination of phthalate-containing plasticizers in the production of plasticized PVC. There is therefore a requirement for phthalate-free plasticizers which achieve the performance level of phthalate-containing plasticizers in relation to processability and service properties.

For the purposes of the present invention, phthalate-free plasticizers are plasticizers which comprise no dialkyl phthalate, in particular plasticizers which comprise less than 0.1% by weight of dialkyl phthalate.

Elimination of phthalate-containing plasticizer is also a demand now placed upon adhesion promoter preparations which comprise plasticizer, in particular for sensitive applications, such as toys or baby products. There is therefore a major requirement for adhesion promoter preparations which comprise no phthalates but nevertheless have the good adhesion properties of phthalate-containing adhesion promoter preparations of the prior art. A further demand is that the preparations are clear and free from solids, comprise no volatile solvents and have viscosity smaller than 30 000 mPas at 23° C., for good processability. Residual content of diisocyanates is to be less than 1.0% by weight. There has hitherto been no description of a combination of all of these product properties in the prior art.

For example, the adhesion promoter preparations described in WO 2005 70984 A1 and based on diisononyl phthalate are no longer suitable for sensitive applications. U.S. Pat. No. 4,115,373 A1 and EP 1 378 529 A1 (U.S. Pat. No. 6,936,678 B2) claim that isocyanurates which contain isocyanate groups and which are suitable as adhesion promoters and which are based on TDI can be prepared in any desired solvents, among which are phthalate-free plasticizers. However, the comparative examples set out below show that it is certainly not true that all phthalate-free plasticizers lead to adhesion promoter preparations which meet the requirements described. DE 30 41 732 A1 (U.S. Pat. No. 4,518,729 A) describes, as adhesion promoters, suitable solutions of isocyanurates which contain isocyanate groups but which are prepared from MDI. These solutions are unsuitable, for the abovementioned reasons.

It was therefore an object of the present invention to provide preparations of isocyanurates which contain isocyanate groups and which are suitable as adhesion promoters, where, although the preparations comprise phthalate-free plasticizers, the level of their mechanical properties, e.g. bond strengths, is the same as that of the phthalate-containing adhesion promoter preparations of WO 2005 70984 A1. The isocyanurates which contain isocyanate groups are to be based on industrially available isomer mixtures of TDI, and in particular the use of pure 2,4-TDI is to be avoided for economic reasons. The preparations are to be clear, and their viscosity is to be <30 000 mPas at 23° C., and their content of free TDI (all isomers) is to be <1.0% by weight.

SUMMARY OF THE INVENTION

This object is achieved via preparations of isocyanurates which contain isocyanate groups and whose viscosity is <30 000 mPas at 23° C. and whose content of free TDI is ≦1.0% by weight (total of all TDI isomers), characterized in that they comprise A) from 15 to 50% by weight of isocyanurates which contain isocyanate groups and which have been prepared from a mixture of isomeric diisocyanatotoluenes comprising from 65 to 95% by weight of 2,4-diisocyanatotoluene and from 5 to 35% by weight of 2,6-diisocyanatotoluene with catalysis by phenolic catalysts containing dialkylamino groups and in the absence of aliphatic hydroxy and/or urethane groups, and B) from 85 to 50% by weight of phthalate-free plasticizers containing aryl alkanesulphonate.

In one preferred embodiment of the invention, the preparations comprise from 20 to 35% by weight of isocyanurates which contain isocyanate groups and from 80 to 65% by weight of phthalate-free plasticizers containing aryl alkanesulphonate.

For preparation of component A), industrially available mixtures in essence composed of 2,4-TDI and 2,6-TDI are used. The TDI isomer mixtures preferably comprise from 75 to 85% by weight of 2,4-TDI in a mixture with from 15 to 25% by weight of 2,6-TDI. The product Desmodur® T80 obtainable from Bayer Material Science AG is an example of these TDI isomer mixtures whose use is preferred.

For preparation of component A), phenolic catalysts containing dialkylamino groups are moreover used, these being well known to the person skilled in the art as Mannich bases. DE 25 51 634 A1 (U.S. Pat. No. 4,115,373 A) and WO 2005 70984 A1 describe by way of example the synthesis of suitable Mannich bases.

Component A) is prepared by trimerization of the diisocyanate mixtures by processes known per se, these being as described by way of example in WO 2005 70984 A1. The trimerization is advantageously carried out in the presence of the plasticizer component B). The trimerization reaction takes place in a temperature range from 40 to 140° C., preferably from 40 to 80° C. When the content of free TDI in the reaction mixture is below 1.0% by weight, the trimerization is terminated by thermal decomposition of the catalyst or else preferably by addition of a catalyst poison. The product then comprises from 3 to 7% by weight of isocyanate groups.

Catalyst poisons suitable for the termination of the trimerization reaction are acids or acid derivatives, for example perfluorobutanesulphonic acid, propionic acid, the isomeric phthaloyl chlorides, benzoic acid or benzoyl chloride, or else quaternizing agents, for example methyl para-toluenesulphonate, diethyl sulphate, or mono- or diesters of phosphoric acid. Methyl para-toluenesulphonate is preferably used as catalyst poison.

According to the invention, the phthalate-free plasticizers of component B) which comprise aryl alkanesulphonate comprise <0.1% by weight of dialkyl phthalate and >0.1% of aryl alkanesulphonate. In one preferred embodiment of the invention, phthalate-free plasticizers with >90% by weight of aryl alkanesulphonate are used as component B). The aryl alkanesulphonates derive from primary or secondary $C_6$-$C_{20}$-alkanesulphonic acids or mixtures of these sulphonic acids. The aryl radicals present in the aryl alkanesulphonates are phenyl, phenyl substituted with from one to five $C_1$-$C_{20}$-alkyl radicals, or phenyl substituted with a $C_6$-$C_{10}$-aryl radical. A mixture of phenyl alkanesulphonates is particularly preferably present as component B). These mixtures are readily industrially available, examples being the products Mesamoll® or Mesamoll® II from Lanxess Deutschland GmbH.

The inventive preparations are clear, slightly yellowish liquids, which even after some weeks of storage have no tendency either towards crystallization or towards formation of precipitates, or phase separation. They also feature extremely low content of free TDI, even after storage, and this is a particular advantage of the inventive preparations, because of the relatively low boiling point of this toxicologically hazardous diisocyanate.

It was unexpected that specifically the combination essential to the invention of plasticizer, catalyst and maximum amount of 2,6-TDI, with no hydroxy compounds present, would provide adhesion promoter preparations with the properties demanded, since according to the prior art the best way of preparing preparations which are suitable as adhesion promoters and comprise isocyanurates which contain isocyanate groups is trimerization of diisocyanates in the plasticizer, and the progress of the trimerization reaction is affected not only by the catalyst but also by way of example by the plasticizer used, the isomer composition of the TDI, or any compounds present during the reaction, for example those containing hydroxy groups. Comparative Examples 2 and 3 set out below actually show that the object underlying this invention cannot be achieved using randomly selected phthalate-free plasticizers.

The inventive preparations are suitable as adhesion promoters for plasticized PVC and in particular as adhesion-promoting additions for PVC plastisols. The inventive preparations are particularly advantageously used as adhesion promoters between substrates composed of synthetic fibres having groups reactive towards isocyanate groups, e.g. polyamide fibres or polyester fibres, and PVC plastisols or flexible-PVC melts. The inventive solutions can, of course, also be used to improve the adhesion of plasticized PVC or of PVC plastisols to sheet-like substrates, for example to foils.

The present invention therefore further provides for the use of inventive preparations as adhesion promoters for coating compositions based on plasticized PVC.

An example of a possible procedure in the inventive use of the inventive preparations applies the inventive preparations to the substrates to be coated by printing, knifing, screen methods or spraying, or dip-coating. As a function of the product to be produced, one or more adhesion-promoter-free PVC layers is/are applied, e.g. in the form of plastisols or by extrusion coating or by hot melt coating or by lamination, to the resultant pretreated substrate surfaces. The inventive preparations can also particularly preferably be added to a PVC plastisol prior to its application.

The amounts normally used of the inventive preparations are such that, based on plasticizer-free PVC of the coating composition, the amount present of isocyanurates which contain isocyanate groups is from 0.5 to 200% by weight, preferably from 2 to 30% by weight. However, it is also possible to use any desired other amounts appropriate to the respective application sector of the inventive solutions.

The production of finished layers, i.e. the reaction of the isocyanate groups of the adhesion promoter with the substrate, and the gelling of the PVC layer, takes place independently of the application mode in the usual way at relatively high temperatures, the temperatures used being from 110 to 210° C. as a function of the composition of the PVC layers.

The present invention further provides coatings and coated substrates for textiles or fabrics, which are obtainable using the adhesion promoter preparations described above. The inventive preparations are suitable as adhesion promoters for coatings based on plasticized PVC, in particular for the production of tarpaulins, of billboards, of air-supported structures and of other textile structures, of flexible containers, of polygonal roofs, of awnings, of protective apparel, of conveyor belts, of flock carpets or of foamed synthetic leather. The inventive preparations have particularly good suitability as added adhesion-promoting agents in the coating of substrates having groups reactive towards isocyanate groups, in particular in the coating of yarns, mats and fabrics composed of polyester fibres or of polyamide fibres.

The examples below provide further illustration of the invention, but there is no intention that the invention be restricted thereby.

It will be understood that the specification and examples are illustrative but not limitative of the present invention and that other embodiments within the spirit and scope of the invention will suggest themselves to those skilled in the art.

EXAMPLES

All parts and percentages are based on weight unless otherwise stated.

Product properties determined were solids content (thick-layer method: lid, 1 g of specimen, 1 h 125° C., convection oven, method based on DIN EN ISO 3251), viscosity at 23° C. (VT550 rotary viscometer from Haake GmbH, Karlsruhe, Germany), and also content of free TDI (gas chromatography, Hewlett Packard 5890 to DIN ISO 55956). Isocyanate content was determined to EN ISO 11909.

Starting Materials

Desmodur® T80: TDI isomer mixture composed of 80% by weight of 2,4-TDI and 20% by weight of 2,6-TDI, Bayer Material Science AG.
Vestinol® 9 DINP: diisononyl phthalate, Oxeno GmbH.
Vestinol® AH: di-2-ethylhexyl phthalate, Oxeno GmbH.
Adimoll® DO: di-2-ethylhexyl adipate, Lanxess Deutschland GmbH.
Benzoflex® 2088: mixture composed of diethylene glycol dibenzoate, triethylene glycol dibenzoate and dipropylene glycol dibenzoate, Velsicol Chemical Corp.
Mesamoll®: phenyl alkanesulphonate, Lanxess Deutschland GmbH.
Mesamoll® II: phenyl alkanesulphonate with ≦0.25% by weight of volatile paraffinic compounds, Lanxess Deutschland GmbH.
Catalyst (preparation according to DE 24 52 532 A1): 188 parts by weight of bisphenol A were heated to 80° C. with 720 parts of a 25% strength aqueous dimethylamine solution and with 425 parts by weight of a 40% strength aqueous formaldehyde solution for two hours. After cooling, the organic phase was separated off and concentrated at 90° C. and 15 mbar. The residue was taken up in a mixture composed of equal parts by volume of butyl acetate and xylene, and the resultant catalyst solution therefore comprised 30% by weight of the desired Mannich base. The quantitative data in the examples below are based on this catalyst solution.

Comparative Example 1 (Non-Inventive)

180 parts of Desmodur® T80 were trimerized at 45° C. in 489 parts of Vestinol® 9 DINP with 7.85 parts of the catalyst solution. After 84 hours, the reaction was interrupted by adding 4.65 parts of methyl para-toluenesulphonate, and stirring of the mixture was continued for one hour at from 60 to 70° C. The solids content was adjusted to 27% by adding 13.4 parts of Vestinol® 9 DINP. This gave a clear solution with isocyanate content of 4.7%, with viscosity of 5700 mPas at 23° C. and with 0.16% of free TDI content.

Comparative Example 2 (Non-Inventive)

180 parts of Desmodur® T80 were trimerized at 45° C. in 414 parts of Adimoll® DO with 2.2 parts of the catalyst solution. After five hours, the reaction was interrupted by adding a terminator, since severe clouding occurred and the product obtained was therefore not homogeneous.

Comparative Example 3 (Non-Inventive)

180 parts of Desmodur® T80 were trimerized at 45° C. in 414 parts of Benzoflex® 2088 with 1.8 parts of the catalyst solution. After 84 hours, the reaction was interrupted by adding 1.65 parts of methyl para-toluenesulphonate, and stirring of the mixture was continued for one hour at from 60 to 70° C. This gave a clear solution with isocyanate content of 4.8%, with viscosity >200 000 mPas at 23° C. and with 1.09% of free TDI content.

Comparative Example 1 corresponds to Example 2 of EP 1 711 546 A1 and serves to permit comparison of the properties of the inventive adhesion promoter preparations with the prior art. As shown by the non-inventive Comparison Examples 2 and 3, the selection of the solvent has a decisive effect on the result of trimerization. This means that the desired property combination cannot be achieved by using the phthalate-free plasticizers described in the prior art, e.g. di-2-ethylhexyl adipate or alkylene glycol dibenzoate mixtures.

Inventive Example 1

180 parts of Desmodur® T80 were trimerized at 45° C in 489 parts of Mesamoll® with 7.85 parts of the catalyst solution. After 84 hours, the reaction was interrupted by adding 4.65 parts of methyl para-toluenesulphonate, and stirring of the mixture was continued for one hour at from 60 to 70° C. The solids content was about 27%. This gave a clear solution with isocyanate content of 5.3%, with viscosity of 10 400 mPas at 23° C., and with 0.78% of free TDI content.

Inventive Example 2

180 parts of Desmodur® T80 were trimerized at 50° C. in 420 parts of Mesamoll® II with 7.85 parts of the catalyst solution. After 84 hours, the reaction was interrupted by adding 4.65 parts of methyl para-toluenesulphonate, and stirring of the mixture was continued for one hour at from 60 to 70° C. The solids content was adjusted to 26% by adding Mesamoll® II. This gave a clear solution with isocyanate content of 4.8%, with viscosity of 11 600 mPas at 23° C., and with 0.25% of free TDI content.

Performance Testing and Test Results

Polyester fabric was provided with a PVC plastisol/adhesion promoter coating in a test system approximating to industrial conditions. The bond strength of this coating was then determined on a standardized test strip. For this, a knife was used to apply an adhesion coat comprising adhesion promoter and two adhesion-promoter-free topcoats using an otherwise identical composition to polyester fabric. These coatings were fully gelled in an oven and used for further testing. Testing for bond strength involved peeling a few centimetres of the coating from the fabric in order to permit clamping of the coatings and fabrics in the tensile testing machine, which then further separated the two layers. The first centimetres of the coating are therefore intended to be capable of easy manual separation. This was achieved by using antiadhesive impregnation material (Table 1) over a width of about 5 cm, and a thin layer of this material was applied using a manually operated knife at one end of the fabric.

TABLE 1

| Composition of antiadhesive impregnation | |
|---|---|
| Constituent | Amount |
| Cellit ® 900, Bayer AG | 105 parts |
| Ethyl acetate | 595 parts |
| Mesamoll ® | 10 parts |

A material was applied to one side of the fabric, on the side on which the adhesive coat was also subsequently applied.

Prior to further processing, the antiadhesive impregnation material was dried in a fume cupboard.

Test Equipment
Balance: min. precision 0.1 g
Stirrer: high-rotation bar stirrer
Convection ovens: T=140° C. and 175° C.
Manually operated knife, width 150 mm
Knife-over-rubber-blanket coater, width about 45 cm, with sharp-edged knife
Knife-over-rubber-blanket coater, width about 45 cm, with blunt-edged knife
Polyester fabric: Lückenhaus, 1100 dtex, plain 1/1 construction, sett: 9/9 ends/picks per cm
The size of the fabric specimens used for testing was about 40×25 cm.

Preparation of PVC Plastisols

TABLE 2

Composition of PVC plastisol

| Constituent | Description | Amount |
| --- | --- | --- |
| Vestolit ® B 7021 | Pasten-PVC, Vestolit GmbH | 30 parts |
| Vestolit ® E 8001 | Pasten-PVC, Vestolit GmbH | 30 parts |
| Mesamoll ®, Vestinol ® AH | Plasticizers | 40 parts |
| Omyalite ® 95T | Calcium carbonate, Omya Australia | 6 parts |
| Naftovin ® T90 | Stabilizer, Chemson GmbH | 2 parts |
| Bayplast ® Grün 8 GN | Organic colour pigment, Lanxess Deutschland GmbH | 0.2 part |

To prepare the PVC plastisol, the starting materials listed in Table 2 were mixed by stirring for 2.5 hours at maximum rotation rate in a Drais mixer, with water cooling, in vacuo.

Adhesive Coat

The adhesive coat based on above plastisol with varying adhesion promoter contents (see Table 3) was applied to the polyester fabric using a knife-over-rubber-blanket method with sharp-edged knife. The weight applied here was about 100 g/m² and in each case the coating was applied to an area of about 30×20 cm. The adhesive coats were then pregelled by two minutes of storage at 140° C. in a convection oven before the topcoats were applied.

First Topcoat

The first topcoat based on abovementioned plastisol was applied by a knife-over-rubber-blanket method using a blunt-edged knife (weight applied about 850 g/m²), and pregelled by heat conditioning at 140° C. for 1 minute in an oven.

Coating for Reverse Side of Fabric

The subsequent topcoat on the reverse side of the fabrics inhibited tearing and fraying of the fabrics during separation of the layers by the tensile machine. The coating on the reverse side of the fabric was applied using a knife-over-rubber-blanket method with a blunt-edged knife (weight applied about 150 g/m²), and was pregelled by heat-conditioning at 140° C. for 1 minute in an oven.

Second Topcoat

The second topcoat likewise based on the PVC plastisol described above was applied using a knife-over-rubber-blanket method with a blunt-edged knife (weight applied about 1400 g/m²), onto the first pregelled topcoat, and pregelled by heat-conditioning at 140° C. for 2 minutes in an oven.

The complete gelling of all of the layers applied then took place by storage at 175° C. for twelve minutes.

Test specimens of size 5×26 cm were stamped out from the resultant fabric specimens.

Bond strengths were determined on these specimens by means of a Lloyd M 5 K tensile machine. The bond strength values obtained give the force in newtons needed to peel 5 cm of the coating from the backing fabric (peel test). The values stated in Table 3 were obtained by averaging of at least three individual measurements.

TABLE 3

Peel test results

| Adhesion promoter preparation | Amount in adhesive coat | Bond strength |
| --- | --- | --- |
| Comparative Example 1 (non-inventive) | 2% | 170 N/5 cm |
| Comparative Example 1 (non-inventive) | 4% | 181 N/5 cm |
| Comparative Example 1 (non-inventive) | 6% | 212 N/5 cm |
| Inventive Example 1 | 2% | 150 N/5 cm |
| Inventive Example 1 | 4% | 195 N/5 cm |
| Inventive Example 1 | 6% | 223 N/5 cm |
| Inventive Example 2 | 2% | 153 N/5 cm |
| Inventive Example 2 | 4% | 190 N/5 cm |
| Inventive Example 2 | 6% | 206 N/5 cm |

As shown by the test results for Inventive Examples 1 and 2, the use of the inventive phthalate-free adhesion promoter preparations gives bond strength values similar to those achieved using the phthalate-containing adhesion promoter preparation of the prior art (Comparative Example 1). The adhesion promoters of Comparative Examples 2 and 3 were not suitable for further processing, since these were either cloudy (Comparative Example 2) or too viscous (Comparative Example 3) to give homogeneous coatings.

What is claimed is:

1. An isocyanurate preparation containing isocyanate groups and having a viscosity <30 000 mPas at 23° C. and having a content of free diisocyanatotoluene ≦1.0% by weight (total of all diisocyanatotoluene isomers), comprising
   A) from 15 to 50% by weight of isocyanurates which contain isocyanate groups and which have been prepared from a mixture of isomeric diisocyanatotoluenes comprising from 65 to 95% by weight of 2,4-diisocyanatotoluene and from 5 to 35% by weight of 2,6-diisocyanato-toluene with catalysis by phenolic catalysts containing dialkylamino groups and in the absence of aliphatic hydroxy and/or urethane groups, and
   B) from 85 to 50% by weight of phthalate-free plasticizers containing a mixture of phenyl alkanesulphonates.

2. A preparation according to Claim 1, comprising from 20 to 35% by weight of isocyanurates having isocyanate groups and from 80 to 65% by weight of phthalate-free plasticizers containing a mixture of phenyl alkanesulphonates.

3. A preparation according to Claim 1, wherein the isocyanurates are prepared from a mixture of from 75 to 85% by weight of 2,4-diisocyanatotoluene and from 15 to 25% by weight of 2,6-diisocyanatotoluene.

4. A preparation according to claim 1, wherein the phthalate-free plasticizers containing >90% by weight of a mixture of phenyl alkanesulphonates.

5. A method of promoting adhesion of a substrate comprising using preparations according to claim 1 for coating compositions based on plasticized polyvinyl chloride.

6. A method of promoting adhesion of substrates including tarpaulins, billboards, air-supported structures and other textile structures, flexible containers, polygonal roofs, awnings, protective apparel, conveyor belts, flock carpets or foamed synthetic leather comprising applying preparations according to claim 1 to the substrate.

7. A coating for textiles or fabrics comprising preparations according to claim 1.

8. A substrate coated with coatings according to claim 7.

9. A substrate according to claim 8 comprising textile polyester fabrics or textile polyamide fabrics.

* * * * *